United States Patent
Yangdai et al.

(10) Patent No.: US 11,311,182 B2
(45) Date of Patent: Apr. 26, 2022

(54) CAPSULE ENDOSCOPE SYSTEM, AUTOMATIC FRAME RATE ADJUSTMENT METHOD THEREOF AND COMPUTER READABLE STORAGE MEDIUM

(71) Applicants: ANKON TECHNOLOGIES CO., LTD, Wuhan (CN); ANX IP HOLDING PTE. LTD., Singapore (SG)

(72) Inventors: Tianyi Yangdai, Wuhan (CN); Yi Li, Wuhan (CN); Qinghua Zhou, Wuhan (CN); Yanli Liu, Wuhan (CN); Rong Wang, Wuhan (CN); Hao Liu, Wuhan (CN); Xinhong Wang, San Diego, CA (US)

(73) Assignees: ANKON TECHNOLOGIES CO., LTD, Wuhan (CN); ANX IP HOLDING PTE. LTD., Singapore (SG)

( * ) Notice: Subject to any disclaimer, the term of this patent is extended or adjusted under 35 U.S.C. 154(b) by 0 days.

(21) Appl. No.: 17/128,116

(22) Filed: Dec. 20, 2020

(65) Prior Publication Data
US 2021/0195102 A1 Jun. 24, 2021

(30) Foreign Application Priority Data
Dec. 20, 2019 (CN) .......................... 201911328024.9

(51) Int. Cl.
*A61B 1/04* (2006.01)
*H04N 5/232* (2006.01)

(52) U.S. Cl.
CPC ......... *A61B 1/041* (2013.01); *H04N 5/23232* (2013.01); *H04N 5/23251* (2013.01)

(58) Field of Classification Search
CPC ..................................... A61B 1/041
See application file for complete search history.

(56) References Cited

U.S. PATENT DOCUMENTS

| | | | |
|---|---|---|---|
| 2003/0139661 A1* | 7/2003 | Kimchy | A61B 8/12 600/407 |
| 2005/0183733 A1* | 8/2005 | Kawano | A61B 1/041 128/899 |

(Continued)

FOREIGN PATENT DOCUMENTS

| | | |
|---|---|---|
| CN | 101674769 A | 5/2011 |
| CN | 102048519 A | 5/2011 |

(Continued)

*Primary Examiner* — David N Werner
(74) *Attorney, Agent, or Firm* — Treasure IP Group, LLC

(57) ABSTRACT

The present invention discloses a capsule endoscope system, an automatic frame rate adjustment method thereof and a computer readable storage medium. The automatic frame rate adjustment method includes: receiving a first acceleration information $a_c(t)$ sensed by a first acceleration sensor in a capsule endoscope; receiving a second acceleration information $a_m(t)$ sensed by a second acceleration sensor in an external device; calculating and comparing the first acceleration information $a_c(t)$ and the second acceleration information $a_m(t)$ to obtain the relative motion amplitude statem (t) between the capsule endoscope and the external device; adjusting the frame rate of the capsule endoscope according to the relative motion amplitude statem(t), where, the larger the relative motion amplitude statem(t), the larger the frame rate $F_0(t)$.

13 Claims, 1 Drawing Sheet

(56) References Cited

U.S. PATENT DOCUMENTS

| | | | |
|---|---|---|---|
| 2009/0012357 A1* | 1/2009 | Suzushima | A61B 5/065 600/109 |
| 2009/0299142 A1* | 12/2009 | Uchiyama | A61B 1/00057 600/118 |
| 2011/0034766 A1* | 2/2011 | Tanaka | A61B 34/72 600/106 |
| 2011/0184690 A1* | 7/2011 | Iida | G06F 3/011 702/150 |
| 2012/0253200 A1* | 10/2012 | Stolka | A61B 90/13 600/459 |
| 2012/0271104 A1* | 10/2012 | Khait | A61B 1/041 600/109 |
| 2013/0201310 A1* | 8/2013 | Jung | H04N 5/2258 348/65 |
| 2013/0261410 A1* | 10/2013 | Davenport | A61B 5/1114 600/302 |
| 2014/0155709 A1* | 6/2014 | Ikai | A61B 5/073 600/302 |
| 2015/0297067 A1* | 10/2015 | Yanagidate | A61B 5/06 600/109 |
| 2017/0127922 A1* | 5/2017 | Godo | A61B 1/00158 |
| 2017/0231470 A1* | 8/2017 | Yanagidate | A61B 1/0002 600/118 |
| 2017/0340242 A1* | 11/2017 | Duan | A61B 1/045 |
| 2018/0084976 A1* | 3/2018 | Duan | A61B 34/73 |
| 2019/0298159 A1* | 10/2019 | Kimura | A61B 1/041 |
| 2021/0068638 A1* | 3/2021 | Yangdai | A61B 1/041 |

FOREIGN PATENT DOCUMENTS

| | | | |
|---|---|---|---|
| CN | 104955377 B | 7/2017 | |
| CN | 107669236 A | 2/2018 | |
| CN | 110575119 A | 12/2019 | |
| CN | 110897595 A | 3/2020 | |
| EP | 2335554 A1 * | 6/2011 | A61B 5/6852 |
| JP | 2005185644 A * | 7/2005 | A61B 1/00156 |
| JP | 2015204948 A * | 11/2015 | A61B 1/00181 |

* cited by examiner

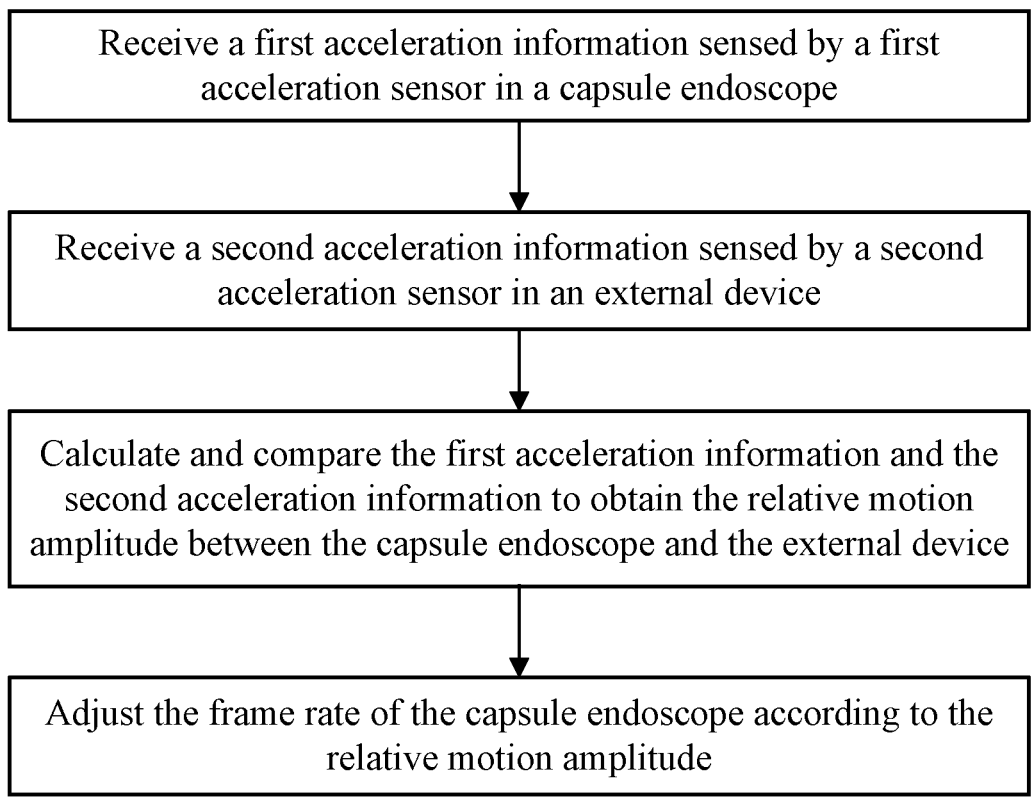

CAPSULE ENDOSCOPE SYSTEM, AUTOMATIC FRAME RATE ADJUSTMENT METHOD THEREOF AND COMPUTER READABLE STORAGE MEDIUM

CROSS-REFERENCE OF RELATED APPLICATIONS

The application claims priority to Chinese Patent Application No. 201911328024.9 filed on Dec. 20, 2019, the contents of which are incorporated by reference herein.

FIELD OF INVENTION

The present invention relates to a capsule endoscopy technique, and more particularly to a capsule endoscope system, an automatic frame rate adjustment method thereof and a computer readable storage medium.

BACKGROUND

As a swallowable device, capsule endoscope has been widely used in gastrointestinal examinations. It is powered by an internal battery and relies on a camera module to take images of the gastrointestinal tract, which are transmitted wirelessly outside the body. Due to limitations such as battery power, the total examination time of a capsule endoscope is usually 8 to 14 hours, and the total number of images taken is 30,000 to 100,000. Therefore, the average frame rate is usually 1~2 fps (frame per second), and it can reach 4~8 fps or even 10~30 fps in a short time. As a result, this creates two problems:

The higher the frame rate, the smoother the video, and the lower the probability of missing images. However, in actual use, the capsule endoscope is powered by a battery which has limited power, and is difficult to support 8 to 14 hours of taking images at a high frame rate. Therefore, in the case of insufficient frame rate, there is a risk of missing images.

Most of the time, the capsule endoscope moves slowly in the digestive tract, and the images taken during the time have so high similarity that a large number of duplicate and redundant images are present, which increases the burden on the review doctor and decreases the review efficiency.

In order to solve the problems, it is necessary to increase the frame rate of capsule endoscope on the one hand, and to reduce the duplicate images taken by the capsule endoscope on the other. Therefore, it is necessary to design a method to automatically adjust the frame rate according to the actual movement of the capsule endoscope. That is, when the capsule endoscope is still or slowly moving relative to the human body, the frame rate is decreased to reduce redundant images and save power; and when the capsule is moving violently relative to the human body, the frame rate is increased to reduce missing images.

At present, there are some published patents to solve the above problems, for example:

Chinese Patent Publication No. CN104955377B, this patent uses an acceleration sensor in a capsule to obtain acceleration information of the capsule, and then uses a signal processing method to determine the movement amplitude and mode of the capsule, thereby adjusting the frame rate. However, using individual acceleration sensor information to determine the motion state of the capsule makes it difficult to rule out the influence of human motion: when the body is moving, the capsule may still be relatively stationary or move in a small amplitude relative to the body, resulting in an examination error.

Chinese Patent Publication No. CN102048519A, this patent application sets up a coil and a current sensor inside the capsule to obtain a motion signal of the capsule by sensing the magnetic field information from the external magnetic field generator, thereby adjusting the frame rate. However, this method relies on the external magnetic field generator, and a system of the generator is complex and not suitable for making a portable device.

Chinese Patent Publication No. CN101674769A, this patent application determines the movement speed of the capsule by calculating the similarity between captured images, or locates the capsule by detecting the strength of wireless signal, thereby adjusting the frame rate. However, the determination is based on image similarity, which requires a large number of calculations, and certain computing power of the equipment. Also, there is a lag in the image-based adjustment of frame rate. For example, if there is a large difference between two neighboring frames, an omission may have already occurred. On the other hand, the accuracy of wireless positioning is low, with errors often reaching the order of centimeters or more, making it prone to erroneous determination and low control accuracy.

Chinese Patent Publication No. CN107669236A, this patent application adjusts the frame rate by providing a six-axis inertial sensor, including an angular velocimeter and accelerometer, in both the capsule and the external data recorder, and calculating the degree of attitude change of the capsule relative to the data recorder. However, the six-axis inertial sensor has high power consumption, and the attitude solution error accumulates over time. Moreover, even when the relative attitude of the capsule and the external data recorder is unchanged, it does not mean that there is no relative motion between the two, so the method still has some drawbacks.

Therefore, it is necessary to design a new capsule endoscope system, an automatic frame rate adjustment method thereof and a computer readable storage medium.

SUMMARY OF THE INVENTION

The present invention discloses an automatic frame rate adjustment method for capsule endoscope system, the method comprising:

receiving a first acceleration information $a_c(t)$ sensed by a first acceleration sensor in a capsule endoscope;

receiving a second acceleration information $a_m(t)$ sensed by a second acceleration sensor in an external device;

calculating and comparing the first acceleration information $a_c(t)$ and the second acceleration information $a_m(t)$ to obtain the relative motion amplitude statem(t) between the capsule endoscope and the external device;

adjusting the frame rate of the capsule endoscope according to the relative motion amplitude statem (t), wherein the larger the relative motion amplitude statem(t), the larger the camera frame rate $F_0(t)$.

In an embodiment, the step "calculating and comparing the first acceleration information $a_c(t)$ and the second acceleration information $a_m(t)$ to obtain the relative motion amplitude statem(t) between the capsule endoscope and the external device" comprises:

performing a difference operation on the first acceleration information $a_c(t)$ to obtain a first acceleration difference value $d_c(t)$, and performing a difference operation on the second acceleration information $a_m(t)$ to obtain a second acceleration difference value $d_m(t)$;

calculating the modulus of the first acceleration difference value $d_c(t)$ and recording it as a first differential modulus Mc(t)=|$d_c$(t)|, calculating the modulus of the second acceleration difference value $d_m$(t) and recording it as a second differential modulus Mm(t)=|$d_m$(t)|;

calculating the mean value $\overline{Mc(t)}$ of the first differential modulus Mc(t), and calculating the mean value $\overline{Mm(t)}$ of the second differential modulus Mm(t);

determining the relative motion amplitude statem(t)=0 when the first acceleration sensor is stationary; determining the relative motion amplitude statem(t)=|$\overline{Mc(t)}$-$\overline{Mm(t)}$| when the first acceleration sensor is not stationary.

In an embodiment, the step "performing a difference operation on the first acceleration information $a_c$(t) to obtain a first acceleration difference value $d_c$(t), and performing a difference operation on the second acceleration information $a_m$(t) to obtain a second acceleration difference value $d_m$(t)" comprises:

obtaining the relationship between the first acceleration information $a_c$(t) of the first acceleration sensor and the actual output $s_c$(t), $$a_c(t)=ks_c(t)+b_c$$

obtaining the relationship between the second acceleration information $a_m$(t) of the second acceleration sensor and the actual output $s_m$(t), $$a_m(t)=ks_m(t)+b_m$$

wherein, k is the conversion coefficient, $b_c$ and $b_m$ are zero drift;

obtaining the sampling interval Δt of the first acceleration sensor, and obtaining the acceleration difference value dc(t) of the actual acceleration $a_c$(t) at two adjacent moments according to the sampling interval Δt, $$dc(t)=(a_c(t)-a_c(t-\Delta t))/\Delta t;$$

obtaining the sampling interval Δt of the second acceleration sensor, and obtaining the acceleration difference value dm(t) of the actual acceleration $a_m$(t) at two adjacent moments according to the sampling interval Δt, $$dm(t)=(a_m(t)-a_m(t-\Delta t))/\Delta t;$$

calculating the relationship between the acceleration difference value dc(t) of the first acceleration sensor and the actual output $s_c$(t), $$dc(t)=k(s_c(t)-s_c(t-\Delta t));$$

calculating the relationship between the acceleration difference value dm(t) of the second acceleration sensor and the actual output $s_m$(t), $$dm(t)=k(s_m(t)-s_m(t-\Delta t)).$$

In an embodiment, the step "calculating the mean value $\overline{Mc(t)}$ of the first differential modulus Mc(t), and calculating the mean value $\overline{Mm(t)}$ of the second differential modulus Mm(t)" comprises:

selecting a window with a width of L, calculating the mean value $\overline{Mc(t)}$ of the first differential modulus Mc(t) in the window, $$\overline{Mc(t)}=\text{mean}(Mc(t-L:t)),$$

and calculating the mean value $\overline{Mm(t)}$ of the second differential modulus Mm(t) in the window, $$\overline{Mm(t)}=\text{mean}(Mm(t-L:t)).$$

In an embodiment, after the step "calculating the mean value $\overline{Mc(t)}$ of the first differential modulus Mc(t), and calculating the mean value $\overline{Mm(t)}$ of the second differential modulus Mm(t)" further comprises:

presetting a dynamic threshold τ, determining that first acceleration sensor is stationary when the mean value $\overline{Mc(t)}$ of the first differential modulus Mc(t) is not greater than the dynamic threshold τ, and determining that the first acceleration sensor is not stationary when the mean value $\overline{Mc(t)}$ of the first differential modulus Mc(t) is greater than the dynamic threshold τ.

In an embodiment, the range of the dynamic threshold τ is 0.005~0.01 m·s$^{-2}$.

In an embodiment, after the step "determining the relative motion amplitude statem(t)=|$\overline{Mc(t)}$-$\overline{Mm(t)}$|" further comprises:

correcting the waveform of the relative motion amplitude statem(t);

wherein the step "correcting the waveform of the relative motion amplitude statem(t)" comprises:

selecting a window with a width of L;

calculating the difference value dMc(h) of the first differential modulus Mc(t) in the window, and $$dMc(h)=Mc(t-(L-1)\Delta t+h\Delta t)-Mc(t-(L-1)\Delta t+(h-1)\Delta t),$$
$$h=1,2\ldots,L-1;$$

calculating the difference value dMm(h) of the second differential modulus Mm(t) in the window, and $$dMm(h)=Mm(t-(L-1)\Delta t+h\Delta t)-Mm(t-(L-1)\Delta t+(h-1)\Delta t), h=1,2\ldots,L-1;$$

binarizing the difference value dMc(h) of the first differential modulus Mc(t) in the window and the difference value dMm(h) of the second differential modulus Mm(t) in the window, and recording them as a first binary difference value dMc(h)' and a second binary difference value dMm(h)', $$dMc(h)^{`} = \begin{cases} 0, & dMc(h) \leq 0 \\ 1, & dMc(h) > 0 \end{cases}, dMm(h)^{`} = \begin{cases} 0, & dMm(h) \leq 0 \\ 1, & dMm(h) > 0 \end{cases};$$

calculating the degree of similarity $R_p$ between the first binary difference value dMc(h)' and the second binary difference value dMm(h)', 0≤$R_p$≤1;

calculating the waveform comparison and correction item P(t) of the waveform, $$P(t) = \begin{cases} R_P, & \text{if } R_P < \alpha \\ 1, & \text{if } R_P \geq \alpha \end{cases}, 0 < \alpha < 1;$$

calculating P(t)●statem(t) and recording as a new relative motion amplitude statem(t).

In an embodiment, $R_p=\Sigma_{h=1}^{L-1}(|dMc(h)-dMm(h)|)/(L-1)$.

In an embodiment, the value of α is 0.5.

In an embodiment, the step "adjusting the frame rate of the capsule endoscope according to the relative motion amplitude statem(t)" comprises:

presetting q frame rate levels f1~fq and the range T1~Tq of the relative motion amplitude statem(t) corresponding to the q frame rate levels, wherein, in the range T1~Tq, the value of the relative motion amplitude statem(t) becomes larger, and f1 to fq also becomes larger, sequentially, setting frame rate $F_0(t)$, $$F_0(t) = \begin{cases} f1, & statem(t) \in T_1 \\ f2, & statem(t) \in T_2 \\ \vdots \\ f_q, & statem(t) \in T_q \end{cases}.$$

In an embodiment, q=4, f1 is 1 fps, f2 is 2 fps, f3 is 4 fps, f4 is 8 fps; T1 is statem(t)≤$s_1$, T2 is $s_1$<statem(t)≤$s_2$, T3 is $s_2$<statem(t)≤$s_3$, T4 is statem(t)>$s_3$, where s1 is 0.01 m·s$^{-2}$, s2 is 0.04 m·s$^{-2}$, s3 is 0.10 m·s$^{-2}$.

In an embodiment, the automatic frame rate adjustment method further comprises:

adjusting the number of images taken at different frame rates in a cycle according to the frame rate $F_0(t)$;

wherein the step "adjusting the number of images taken at different frame rates in a cycle according to the frame rate $F_0(t)$" comprises:

obtaining the total number of images taken by the capsule endoscope in each cycle and recording as N(jT), recording the duration of each cycle as TS(s), where, 1≤j≤n, n is the total number of cycles;

calculating and allocating the number of images N1~Nq taken at the frame rates f1~fq, and N1~Nq meet the following conditions:

$$\sum_{i=1}^{q} N_i \leq N(jT),$$
$$\frac{1}{f_1}N_1 + \frac{1}{f_2}N_2 + \ldots + \frac{1}{f_q}N_q \geq T_s.$$

In an embodiment, the automatic frame rate adjustment method further comprises:

allocating the total number of images to be taken for the remaining cycles based on the total number of images actually taken in a cycle;

wherein the step "allocating the total number of images to be taken for the remaining cycles based on the total number of images actually taken in a cycle" comprises:

calculating the total number of images N(jT)' actually taken in the j-th cycle;

calculating the total number of images $N_{maqin}$=N(jT)−N(jT)' remaining to be taken in the j-th cycle;

calculating the total number of images $N(iT)_{new}$ taken in the remaining cycles, $$N(iT)_{new} = \frac{N_{maqin}}{n-j} + N(iT), \ j < i \leq n;$$

N(iT) is the estimated total number of images taken in the original i-th cycle;

calculating again the number of images taken at different frame rates in each cycle.

The present invention further provides a capsule endoscope system. The capsule endoscope system comprises a capsule endoscope and an external device. The external device comprises a memory and a processor. The memory stores computer programs that run on the processor, and the processor executes the computer programs to implement the steps in the automatic frame rate adjustment method as described above.

The present invention further provides a computer-readable storage medium for storing computer programs. The computer programs are executed by the processor to implement the steps in the automatic frame rate adjustment method described above.

In the present invention, acceleration sensors are installed in both the capsule endoscope and the external device to detect the acceleration information of the capsule endoscope and human body, so that the relative motion amplitude of the two can be effectively determined. Also, adjusting frame rate through the relative motion amplitude can effectively eliminate the interference of human motion. The larger the relative motion amplitude is, the faster the capsule endoscope moves, so adjust the frame rate of the camera of the capsule endoscope, i.e., increasing it, to prevent missing images. The smaller the relative motion amplitude is, the slower the capsule moves in human body, so adjust the frame rate of the camera, i.e., decreasing it, to reducing duplicate redundant images.

BRIEF DESCRIPTION OF THE DRAWINGS

FIG. 1 shows an automatic frame rate adjustment method for a capsule endoscope system according to aspects of the present invention.

DETAILED DESCRIPTION

In order to enable those skilled in the art to better understand the technical solutions disclosed, the present invention can be described in detail below with reference to the accompanying drawings and preferred embodiments. However, the embodiments are not intended to limit the invention, and obviously, the described embodiments are only a part of the embodiments of the present invention, but not all of them. All other embodiments obtained by those having ordinary skill in the art without creative work based on the embodiments of the present invention are included in the scope of the present invention.

Referring to FIG. 1, the present invention discloses an automatic frame rate adjustment method for a capsule endoscope system, the method comprising:

receiving a first acceleration information $a_c(t)$ sensed by a first acceleration sensor in a capsule endoscope;

receiving a second acceleration information $a_m(t)$ sensed by a second acceleration sensor in an external device;

calculating and comparing the first acceleration information $a_c(t)$ and the second acceleration information $a_m(t)$ to obtain the relative motion amplitude statem(t) between the capsule endoscope and the external device;

adjusting the frame rate of the camera of the capsule endoscope according to the relative motion amplitude statem(t), wherein, the larger the relative motion amplitude statem(t), the larger the camera frame rate $F_0(t)$.

In the present invention, acceleration sensors are installed in both the capsule endoscope and the external device to detect the acceleration information of the capsule endoscope and human body, so that the relative motion amplitude of the two can be effectively determined. Also, adjusting frame rate through the relative motion amplitude can effectively eliminate the interference of human motion. The larger the relative motion amplitude is, the faster the capsule endoscope moves, so adjust the frame rate of the camera, i.e., increasing it, to prevent missing images. The smaller the relative motion amplitude is, the slower the capsule moves in human body, so adjust the frame rate of the camera, i.e., decreasing it, to reducing duplicate redundant images.

In the present invention, the first acceleration sensor installed in the capsule endoscope and the second acceleration sensor installed in the external device collect data synchronously at the same sampling rate, and come with the same type to ensure synchronization of measurement data between the two. In the embodiment, the first acceleration information detected by the first acceleration sensor is wirelessly transmitted to the external device, then the external device stores the first acceleration information and the second acceleration information that the second acceleration sensor collects, and transmits them together to a calculation module inside the external device for calculating the relative motion amplitude statem(t). And, it is apparent that the acceleration information detected by the acceleration sensors is vector information, and thus the first acceleration information $a_c(t)$ and the second acceleration information $a_m(t)$ are vector information.

In the embodiment, both the first acceleration sensor and the second acceleration sensor can detect acceleration information in three directions, that is, they can collect acceleration information in the X, Y, and Z axes. Assuming that the actual output in the i-axis of the acceleration sensor is $s_i$, the actual acceleration $a_i$ in the axis has a conversion relation as follows:

$$a_i = ks_i + b;$$

where, k is conversion factor, which is related to the range and accuracy of G-sensor. For example, when the range is ±2 g and the accuracy is 16 bits, it is $k = 2 \text{ g} \times 2^{-15} \approx 6 \times 10^{-4} \text{ m·s}^{-2}$. $b(\text{m·s}^{-2})$ is zero drift, which is affected by temperature and individual differences in the acceleration sensors, that is, when the acceleration sensor is stationary, the mean value of output is not zero, and this non-zero mean value is zero drift. In the embodiment, as mentioned above, in the capsule endoscope system, the capsule endoscope and the external device comprise the acceleration sensors of same type or same performance indicators, the difference of the conversion factor k is small, only when the measurement data is large, the difference is significant. However, the zero-drift value varies significantly with the acceleration sensor, and if not corrected, can cause two acceleration sensors in the same state to output different values. Specifically, the details are described below.

The step "calculating and comparing the first acceleration information $a_c(t)$ and the second acceleration information $a_m(t)$ to obtain the relative motion amplitude statem(t) between the capsule endoscope and the external device" comprises:

performing a difference operation on the first acceleration information $a_c(t)$ to obtain a first acceleration difference value $d_c(t)$, and performing a difference operation on the second acceleration information $a_m(t)$ to obtain a second acceleration difference value $d_m(t)$;

calculating the modulus of the first acceleration difference value $d_c(t)$ and recording it as a first differential modulus $Mc(t) = |d_c(t)|$, calculating the modulus of the second acceleration difference value $d_m(t)$ and recording it as a second differential modulus $Mm(t) = |d_m(t)|$;

calculating the mean value $\overline{Mc(t)}$ of the first differential modulus $Mc(t)$, and calculating the mean value $\overline{Mm(t)}$ of the second differential modulus $Mm(t)$;

determining the relative motion amplitude statem(t)=0 if the first acceleration sensor is stationary; determining the relative motion amplitude statem(t)=$|\overline{Mc(t)} - \overline{Mm(t)}|$ if the first acceleration sensor is not stationary.

In the present invention, when comparing the relative motion amplitude statem(t), as described above, both the first acceleration sensor and the second acceleration sensor detect the acceleration information in three axes (X/Y/Z), so the first acceleration information $a_c(t)$ and the second acceleration information $a_m(t)$ are three-dimensional vectors, and the first acceleration difference value $d_c(t)$ and the second acceleration difference value $d_m(t)$ are also three-dimensional vectors. Furthermore, as described above, since the first acceleration sensor and the second acceleration sensor have different postures corresponding to the coordinate system and different zero drifts, if the acceleration information is used directly, it is still affected by the posture and the zero drift. Therefore, in the present invention, a differential modulus can be used to determine the relative motion amplitude.

Specifically, in the embodiment, the first acceleration difference value $d_c(t)$ and the second acceleration difference value $d_m(t)$ are calculated separately to avoid the influence of zero drift; a modulo operation is performed on the first acceleration difference value $d_c(t)$ and the second acceleration difference value $d_m(t)$ to obtain the first differential modulus $Mc(t)$ and the second differential modulus $Mm(t)$ to eliminate the influence of different postures of the first acceleration sensor and the second acceleration sensor; and the mean value of differential modulus is calculated to weaken the noise influence of the acceleration sensors. In other method, if the zero drift has been corrected in advance, the relative motion amplitude statem(t) can be obtained without calculating the acceleration difference value. Alternatively, if the influence of different postures corresponding to the coordinate system is not taken into account, it is possible to calculate the relative motion magnitude statem(t) without calculating the differential modulus.

Further, the step "performing a difference operation on the first acceleration information $a_c(t)$ to obtain a first acceleration difference value $d_c(t)$, and performing a difference operation on the second acceleration information $a_m(t)$ to obtain a second acceleration difference value $d_m(t)$" comprises:

obtaining the relationship between the first acceleration information $a_c(t)$ of the first acceleration sensor and the actual output $s_c(t)$, $$a_c(t) = ks_c(t) + b_c,$$

obtaining the relationship between the second acceleration information $a_m(t)$ of the second acceleration sensor and the actual output $s_m(t)$, $$a_m(t) = ks_m(t) + b_m,$$

Where, k is the conversion coefficient, $b_c$ and $b_m$ are zero drift;

obtaining the sampling interval $\Delta t$ of the first acceleration sensor, and obtaining the acceleration difference value $d_c(t)$ of the actual acceleration $a_c(t)$ at two adjacent moments according to the sampling interval $\Delta t$, $$dc(t) = (a_c(t) - a_c(t - \Delta t))/\Delta t;$$

obtaining the sampling interval $\Delta t$ of the second acceleration sensor, and obtaining the acceleration difference value dm(t) of the actual acceleration $a_m(t)$ at two adjacent moments according to the sampling interval $\Delta t$, $$dm(t) = (a_m(t) - a_m(t - \Delta t))/\Delta t;$$

calculating the relationship between the acceleration difference value dc(t) of the first acceleration sensor and the actual output $s_c(t)$, $$dc(t) = k(s_c(t) - s_c(t - \Delta t));$$

calculating the relationship between the acceleration difference value dm(t) of the second acceleration sensor and the actual output $s_m(t)$, $$dm(t)=k(s_m(t)-s_m(t-\Delta t)).$$

Where, based on the relationship $a_i=ks_i+b$ between the actual acceleration $a_i$ in a single axis and the actual output $s_i$ in the axis, the relationship between the three-dimensional vectors $a_c(t)$ and $a_m(t)$ and the actual outputs $s_c(t)$ and $s_m(t)$ can be inferred, and through difference calculation, the zero drifts $b_c$ and $b_m$ can be removed. Therefore, the correction operation of the zero drifts of the first acceleration sensor and the second acceleration sensor before use can be avoided, thus reducing the requirements on users.

It should be noted that, as mentioned above, there is inevitably noise in sensor measurement, and noise is an unknown random variable, which approximately obeys Gaussian distribution and has a mean value of about zero, and the standard deviation is proportional to the actual outputs $s_c(t)$ and $s_m(t)$, respectively. But due to a small impact on the overall results, it can be ignored in the above analysis process, and in the subsequent calculation process, other correction methods are still added to correct the sensor measurement noise. In addition, although the first acceleration sensor and the second acceleration sensor used in the present invention are identical in type, a certain difference may still be caused in their conversion factors k. However, in general, the difference in the conversion factors k is small, so in the present invention, the same conversion factor k can be directly used for calculation.

In addition, in the embodiment, the acceleration difference value dc(t) of the actual acceleration $a_c(t)$ at two adjacent moments is obtained according to the sampling interval $\Delta t$. Alternatively, in other embodiments, the objects of the present invention can also be achieved, if instead of taking the acceleration difference value at the two adjacent moments, the acceleration difference value at the two moments that are not adjacent is used.

The sampling interval $\Delta t$ is approximately 30-250 ms, and in the specific embodiment, it is not greater than the minimum interval at which image is taken. If the sampling interval $\Delta t$ is another value, the objects of the present invention can also be achieved. For example, if the maximum frame rate of capsule endoscope is 4 fps, the minimum interval $\Delta t$ for image taking is 250 ms, and $\Delta t \leq 250$ ms can be taken. In a specific capsule endoscope system, the sampling interval $\Delta t$ is fixed, so the acceleration difference values dc(t) and dm(t) can be directly calculated.

Further, the step "calculating the mean value $\overline{Mc(t)}$ of the first differential modulus Mc(t), and calculating the mean value $\overline{Mm(t)}$ of the second differential modulus Mm(t)" comprises:

selecting a window with a width of L, calculating the mean value $\overline{Mc(t)}$ of the first differential modulus Mc(t) in the window, $$\overline{Mc(t)}=\text{mean}(Mc(t-L:t)),$$

and calculating the mean value $\overline{Mm(t)}$ of the second differential modulus Mm(t) in the window, $$\overline{Mm(t)}=\text{mean}(Mm(t-L:t)).$$

In the embodiment, after the first differential modulus Mc(t) and the second differential modulus Mm(t) are obtained, the problem of different postures of the first acceleration sensor and the second acceleration sensor can be solved by the method of modulo operation. In addition, in this step, the mean values of the first differential modulus Mc(t) and the second differential modulus Mm(t) are further calculated to reduce the noise influence of the acceleration sensors.

Specifically, in the embodiment, the size of the window L used in the process of calculating the mean values of the first differential modulus Mc(t) and the second differential modulus Mm(t) is the same, i.e 4~10. In the embodiment, $\overline{Mc(t)}=\text{mean}(Mc(t-L:t))$ refers to the mean value of the first differential modulus Mc(t) at L−1 time points including $t-(L-1)\Delta t, \ldots, t-\Delta t, t$ during time t; similarly, $\overline{Mm(t)}=\text{mean}(Mm(t-L:t))$ refers to the mean value of the second differential modulus Mm(t) at L−1 time points including $t-(L-1)\Delta t, \ldots, t-\Delta t, t$ during time t.

Further, under ideal conditions, if the capsule endoscope is completely stationary, the mean value $\overline{Mc(t)}$ of the first differential modulus Mc(t) should be 0. However, due to some interference factors such as noise, when the capsule endoscope is completely stationary, the mean value $\overline{Mc(t)}$ of the first differential modulus Mc(t) is not identically equal to 0, but has a certain fluctuation, and the fluctuation is approximately between $0.005 \sim 0.01$ m·s$^{-2}$.

Therefore, in the embodiment, after the step "calculating the mean value $\overline{Mc(t)}$ of the first differential modulus Mc(t), and calculating the mean value $\overline{Mm(t)}$ of the second differential modulus Mm(t)" further comprises: presetting a dynamic threshold $\tau$, if the mean value $\overline{Mc(t)}$ of the first differential modulus Mc(t) is not greater than the dynamic threshold $\tau$, determining that the first acceleration sensor is stationary and the relative displacement statem(t) should be 0, and if the mean value $\overline{Mc(t)}$ of the first differential modulus Mc(t) is greater than the dynamic threshold $\tau$, determining that the first acceleration sensor is not stationary. Then, it means that if the mean value $\overline{Mc(t)}$ of the first differential modulus Mc(t) is not greater than the dynamic threshold $\tau$, the relative motion amplitude statem(t)=0, and if the mean value $\overline{Mc(t)}$ of the first differential modulus Mc(t) is greater than the dynamic threshold $\tau$, there should be relative motion between the capsule endoscope and the external device, and the relative motion amplitude $$\text{statem}(t)=|\overline{Mc(t)}-\overline{Mm(t)}|.$$

Further, theoretically, if the capsule endoscope and the external device are relatively stationary, the acceleration waveforms of the two should be identical, and the mean value $\overline{Mc(t)}$ of the first differential modulus Mc(t) and the mean value $\overline{Mm(t)}$ of the second differential modulus Mm(t) should always be the same. However, due to the difference in the sensor noise and the conversion factor k, there is a certain difference in the amplitude of fluctuation between the two, that is, there is a residual error in the above formula statem(t)=|$\overline{Mc(t)}-\overline{Mm(t)}$| and the amplitude of the residual error is positively correlated with the intensity of $\overline{Mc(t)}$ and $\overline{Mm(t)}$. As a result, even if the two are relatively stationary, the calculation result of formula statem(t)=|$\overline{Mc(t)}-\overline{Mm(t)}$| may still have a large value, leading to an erroneous use of high frame rate, wasting battery power, and causing image redundancy. Therefore, it is necessary to correct the waveform of statem(t)=|$\overline{Mc(t)}-\overline{Mm(t)}$|. But, if the requirement for accuracy is not high or the battery power is sufficient, this step can also be omitted to achieve the object of the present invention.

Specifically, after the step "determining the relative motion amplitude statem(t)=|$\overline{Mc(t)}-\overline{Mm(t)}$|" further comprises:

correcting the waveform of the relative motion amplitude statem(t);

The step "correcting the waveform of the relative motion amplitude statem(t)" comprises:

selecting a window with a width of L;

calculating the difference value dMc(h) of the first differential modulus Mc(t) in the window, that is:

$$dMc(h)=Mc(t-(L-1)\Delta t+h\Delta t)-Mc(t-(L-1)\Delta t+(h-1)\Delta t),$$
$$h=1,2\ldots,L-1;$$

calculating the difference value dMm(h) of the second differential modulus Mm(t) in the window, that is:

$$dMm(h)=Mm(t-(L-1)\Delta t+h\Delta t)-Mm(t-(L-1)\Delta t+(h-1)\Delta t),h=1,2\ldots,L-1;$$

binarizing the difference value dMc(h) of the first differential modulus Mc(t) in the window and the difference value dMm(h) of the second differential modulus Mm(t) in the window, and recording them as a first binary difference value dMc(h)' and a second binary difference value dMm(h)', $$dMc(h)' = \begin{cases} 0, & dMc(h) \leq 0 \\ 1, & dMc(h) > 0 \end{cases}, dMm(h)' = \begin{cases} 0, & dMm(h) \leq 0 \\ 1, & dMm(h) > 0 \end{cases};$$

calculating the degree of similarity $R_p$ between the first binary difference value dMc(h)' and the second binary difference value dMm(h)', $0 \leq R_p \leq 1$;

calculating the comparison and correction item P(t) of the waveform, $$P(t) = \begin{cases} R_p, & \text{if } R_p < \alpha \\ 1, & \text{if } R_p \geq \alpha \end{cases}, 0 < \alpha < 1;$$

calculating P(t)●statem(t) and recording as a new relative motion amplitude statem(t).

In the process of correction, a window with a width of L is also selected, and the difference between the two adjacent values in the window is compared.

Since h=1, 2 . . . , L−1, as below, assuming L is 5, the value of dMm(h) is equivalent to:

When h=1, dMm(1)=Mm(t−3Δt)−Mm(t−4Δt);
When h=2, dMm(2)=Mm(t−2Δt)−Mm(t−3Δt);
When h=3, dMm(3)=Mm(t−Δt)−Mm(t−2Δt);
When h=4, dMm(4)=Mm(t)−Mm(t−Δt);

So, in window L, if Mm(t−3Δt)>Mm(t−4Δt), dMm(1)>0, which means that when h=1, the second differential modulus Mm(t) presents a rising edge; if Mm(t−Δt)≤Mm(t−2Δt), dMm(3)≤0, which means that when h=3, the second differential modulus Mm(t) presents on a falling edge. Therefore, in window L, if the previous value is greater than the next value, the waveform can be considered to have a falling edge, and if the previous value is smaller than the next value, the waveform can be considered to have a rising edge.

Then further, binarizing the difference value dMc(h) of the first differential modulus Mc(t) in the window and the difference value dMm(h) of the second differential modulus Mm(t) in the window, to distinguish the fluctuations of waveforms of the difference value dMc(h) of the first differential modulus Mc(t) in the window and the difference value dMm(h) of the second differential modulus Mm(t) in the window.

Therefore, further, by comparing dMc' and dMm', the similarity between the fluctuations of waveforms of the two can be determined. If they are exactly the same, it means that the first acceleration sensor and the second acceleration sensor have synchronized motion, so the relative motion amplitude statem(t) should be 0; if they have high degree of similarity, it means that the motions of the first acceleration sensor and the second acceleration sensor are correlated, the relative motion amplitude statem(t) can be corrected to improve the determination accuracy of final frame rate; if they have quite low degree of similarity, it means that the motions of the first acceleration sensor and the second acceleration sensor are completely uncorrelated, so there is no need to correct the relative motion amplitude statem(t).

Therefore, in the specific embodiment, the waveforms of dMc' and dMm' are further compared and the degree of similarity is determined. Specifically, the degree of similarity $R_p$ between dMc' and dMn' in the window is calculated. $R_p$ describes the degree of similarity between fluctuations of dMc' and dMm'. The greater the value of $R_p$, the less correlation is determined between dMc(h) and dMm(h), and $0 \leq R_p \leq 1$.

Therefore, set a threshold α. If $0 \leq R_p < \alpha$, it means that the waveforms dMc' and dMm' are relatively similar or the same, and it also means that the waveforms of the first differential modulus Mc(t) and the second differential modulus Mm(t) are also relatively similar or the same, so the motion amplitude statem(t) can be corrected accordingly; if $R_p \geq \alpha$, it means that the waveforms dMc' and dMm' are less similar, and it also means that the waveforms of the first differential modulus Mc(t) and the second differential modulus Mm(t) are less similar, and there is no need to correct the motion amplitude statem(t). Since $0 \leq R_p \leq 1$, compare the correction item $0 \leq P(t) < \alpha$ or 1. In the correction process of $0 \leq P(t) < \alpha$, P(t)●statem(t), so the relative motion amplitude statem(t) that is too large can be reduced to make statem(t) more accurate after correction, and the frame rate determination more accurate too.

Further, the degree of similarity R is calculated as follows:

$$R_p = \Sigma_{h=1}^{L-1}(|dMc(h)-dMm(h)|)/(L-1)$$

Also, other ways to calculate the degree of similarity $R_p$ would also meet the requirements of the present invention. Further, the value of α is 0.5, and likewise, if α is any other value, it can also meet the requirements of the present invention as long as it achieves the objects of the present invention.

The calculation method of the relative motion amplitude has been described above, and the adjustment of the frame rate is described in detail below.

The step "adjusting the frame rate of the camera of the capsule endoscope according to the relative motion amplitude statem(t)" comprises:

presetting q frame rate levels f1~fq and the range T1~Tq of the relative motion amplitude corresponding to the q frame rate levels, and setting a frame rate $F_0(t)$, where, in the range T1~Tq, the value of the relative motion amplitude statem(t) becomes larger, and f1 to fq also becomes larger, sequentially, $$F_0(t) = \begin{cases} f1, & statem(t) \in T_1 \\ f2, & statem(t) \in T_2 \\ \vdots \\ f_q, & statem(t) \in T_q \end{cases}.$$

That is, the range of the relative motion amplitude statem(t) is divided into q ranges, and the frame rate $F_0(t)$ in each of the q ranges is different. Then, it is obvious that the larger the value of the relative motion amplitude statem(t), the larger the corresponding frame rate $F_0(t)$. And further, as described above, the sampling interval $\Delta t$ of the acceleration sensor in the present invention is not greater than the minimum interval for image capturing, that is, the sampling rate is not smaller than the highest frame rate for image capturing. Therefore, when the motion amplitude statem(t) is large, and it is determined that the frame rate needs to be increased, the camera can be immediately controlled to take images at a higher frame rate to avoid missing frames.

In the embodiment, specifically, the frame rate has four levels, so q=4, f1 is 1 fps, f2 is 2 fps, f3 is 4 fps, and f4 is 8 fps; T1 is statem(t)$\leq s_1$, T2 is $s_1<$statem(t)$\leq s_2$, T3 is $s_2<$statem(t)$\leq s_3$, T4 is statem(t)$>s_3$, where s1 is 0.01 m·s$^{-2}$, s2 is 0.04 m·s$^{-2}$, s3 is 0.10 m·s$^{-2}$.

However, due to the limited battery power, the capsule endoscope cannot always be in a state of high frame rate, so it is necessary to limit the number of images taken at high frame rate to obtain an effective number of images taken at different frame rates.

Specifically, the automatic frame rate adjustment method further comprises:

adjusting the number of images taken at different frame rates in a cycle according to the frame rate $F_0(t)$;

The step "adjusting the number of images taken at different frame rates in a cycle according to the frame rate $F_0(t)$" comprises:

obtaining the total number of images taken by the capsule endoscope in each cycle and recording as N(jT), recording the duration of each cycle as TS(s), where, $1 \leq j \leq n$, n is the total number of cycles;

calculating and allocating the number of images N1~Nq taken at the frame rates f1~fq, and N1~Nq must meet the following conditions:

$$\sum_{i=1}^{q} N_i \leq N(jT),$$
$$\frac{1}{f_1}N_1 + \frac{1}{f_2}N_2 + \ldots + \frac{1}{f_q}N_q \geq T_s.$$

Assuming that there are n cycles in the image taking process and the total number of images taken in the j-th cycle is N(jT), it is obvious that the total number of images taken at all frame rates in each cycle must be less than the total number of images N(jT), and the total duration of image taking at all frame rates in each cycle must be up to the duration TS(s) of the cycle, so the number of images taken at different frame rates can be calculated.

Specifically, for example, in the specific embodiment, if the capsule endoscope can take a total of 50000 images, the user requires the capsule endoscope to work for 8 hours with a duration of 10 minutes per cycle, in the case of even distribution, the total number of images taken in each cycle is N(jT)=50000/(8×6)≈1042.

In the case of four frame rate levels as described above, $N_1+N_2+N_3+N_4 \leq 1042$, and $$N_1 + \frac{1}{2}N_2 + \frac{1}{4}N_4 \geq 60 \times 10(s).$$

Then, the values of N1~N4 are determined through calculation and determination of N1 to N4.

Specifically, in the embodiment, the reference ratios r1~rq of each frame rate level can be determined based on experience or experiment, so that the specific values of N1~Ng can be determined. Here, the reference ratios r1~rq are used to help calculate N1~Nq. The actual calculated ratios between N1 to Nq are not necessarily equal to r1 to rq, but should be close.

Further, since in actual situations, the frame rate may be always low in one cycle, the number of images actually taken is small, and the redundant images can be allocated to the remaining cycles. Specifically, the automatic frame rate adjustment method further comprises:

allocating the total number of images to be taken for the remaining cycles based on the total number of images actually taken in a cycle;

The step "allocating the total number of images to be taken for the remaining cycles based on the total number of images actually taken in a cycle" comprises:

calculating the total number of images N(jT)' actually taken in the j-th cycle;

calculating the total number of images $N_{maqin}$=N(jT)−N(jT)' remaining to be taken in the j-th cycle;

calculating the total number of images N(iT)$_{new}$ taken in the remaining cycles, $$N(iT)_{new} = \frac{N_{maqin}}{n-j} + N(iT),$$

j<i$\leq$n; N(iT) is the estimated total number of images taken in the original i-th cycle;

calculating again the number of images taken at different frame rates in each cycle.

That is, the total number of images remaining to be taken in one cycle is calculated, and then evenly distributed into other cycles. In addition, the number of images taken at different frame rates can also be recalculated after the quota for total number of images taken in the remaining cycles is obtained.

The present invention further provides a capsule endoscope system. The capsule endoscope system comprises a capsule endoscope and an external device. The external device comprises a memory and a processor. The memory stores computer programs that can run on the processor, and the processor executes the computer programs to implement any step in the automatic frame rate adjustment method as described above, that is, implement any one of the embodiments in the automatic frame rate adjustment method.

In addition, the present invention further provides a computer readable storage medium for storing computer programs. The computer programs are executed by the processor to implement any step in the automatic frame rate adjustment method as described above, that is, implement any one of the embodiments in the automatic frame rate adjustment method.

Therefore, in summary, the present invention provides a capsule endoscope system, an automatic frame rate adjustment method thereof and a computer readable storage medium. Specifically, in the present invention, acceleration sensors are installed in both the capsule endoscope and the external device to detect the acceleration information of the capsule endoscope and human body, so that the relative motion amplitude of the two can be effectively determined. Also, adjusting frame rate through the relative motion amplitude can effectively eliminate the interference of human motion.

Further, in the present invention, the first acceleration difference value $d_c(t)$ and the second acceleration difference value $d_m(t)$ are calculated to avoid the influence of zero drift, and modulo operation is performed on the first acceleration difference value $d_c(t)$ and the second acceleration difference value $d_m(t)$ to exclude the influence of different postures corresponding to the coordinate system, and the mean value of the differential modulus is calculated to reduce the influence of noise, so that the accuracy of the relative motion amplitude in the present invention can be improved.

In addition, by correcting the waveforms of the relative motion amplitude statem(t), it is possible to prevent the first acceleration sensor and the second acceleration sensor from being mistaken for a large relative motion amplitude statem (t) even when they move synchronously. This can make the results more accurate.

Finally, the present invention further provides the calculation of the frame rate levels, the calculation of the number of images taken at different frame rates, and the calculation of the quota for total number of images taken in different cycles, to make the whole method more complete, and further improve the utilization rate of the entire capsule endoscope and reduce image redundancy.

It should be understood that, although the specification is described in terms of embodiments, not every embodiment merely comprises an independent technical solution. This narration in the specification is only for clarity, those skilled in the art should have the specification as a whole, and the technical solutions in each embodiment may also be combined as appropriate to form other embodiments that can be understood by those skilled in the art.

The series of detailed descriptions listed above are only specific descriptions of feasible implementations of the present invention, and are not intended to limit the protection scope of the present invention. On the contrary, any equivalent implementations made without departing from the technical spirit of the present invention, the modifications and variations are possible within the scope of the appended claims.

What is claimed is:

1. An automatic frame rate adjustment method for capsule endoscope system, comprising:
    receiving a first acceleration information $a_c(t)$ sensed by a first acceleration sensor in a capsule endoscope;
    receiving a second acceleration information $a_m(t)$ sensed by a second acceleration sensor in an external device;
    calculating and comparing the first acceleration information $a_c(t)$ and the second acceleration information $a_m(t)$ to obtain the relative motion amplitude statem(t) between the capsule endoscope and the external device;
    adjusting the frame rate of the capsule endoscope according to the relative motion amplitude statem(t), wherein the larger the relative motion amplitude statem(t), the larger the frame rate $F_0(t)$, $$F_0(t) = \begin{cases} f1, & statem(t) \in T_1 \\ f2, & statem(t) \in T_2 \\ \vdots \\ f_q, & statem(t) \in T_q \end{cases}$$

wherein the step "calculating and comparing the first acceleration information $a_c(t)$ and the second acceleration information $a_m(t)$ to obtain the relative motion amplitude statem (t) between the capsule endoscope and the external device" comprises:
    performing a difference operation on the first acceleration information $a_c(t)$ to obtain a first acceleration difference value $d_c(t)$, and performing a difference operation on the second acceleration information $a_m(t)$ to obtain a second acceleration difference value $d_m(t)$;
    calculating the modulus of the first acceleration difference value $d_c(t)$ and recording it as a first differential modulus $Mc(t)=|d_c(t)|$, calculating the modulus of the second acceleration difference value $d_m(t)$ and recording it as a second differential modulus $Mm(t)=|d_m(t)|$;
    calculating the mean value $\overline{Mc(t)}$ of the first differential modulus $Mc(t)$, and calculating the mean value $\overline{Mm(t)}$ of the second differential modulus $Mm(t)$;
    determining the relative motion amplitude statem(t)=0 when the first acceleration sensor is stationary; determining the relative motion amplitude statem(t)=$|\overline{Mc(t)}-\overline{Mm(t)}|$ when the first acceleration sensor is not stationary.

2. The automatic frame rate adjustment method of claim 1, wherein the step "performing a difference operation on the first acceleration information $a_c(t)$ to obtain a first acceleration difference value $d_c(t)$, and performing a difference operation on the second acceleration information $a_m(t)$ to obtain a second acceleration difference value $d_m(t)$" comprises:
    obtaining the relationship between the first acceleration information $a_c(t)$ of the first acceleration sensor and the actual output $s_c(t)$, $$a_c(t)=ks_c(t)+b_c$$

obtaining the relationship between the second acceleration information $a_m(t)$ of the second acceleration sensor and the actual output $s_m(t)$, $$a_m(t)=ks_m(t)+b_m$$

wherein, k is the conversion coefficient, $b_c$ and $b_m$ are zero drift;
    obtaining the sampling interval $\Delta t$ of the first acceleration sensor, and obtaining the acceleration difference value $dc(t)$ of the actual acceleration $a_c(t)$ at two adjacent moments according to the sampling interval $\Delta t$, $$dc(t)=(a_c(t)-a_c(t-\Delta t))/\Delta t;$$

obtaining the sampling interval $\Delta t$ of the second acceleration sensor, and obtaining the acceleration difference value $dm(t)$ of the actual acceleration $a_m(t)$ at two adjacent moments according to the sampling interval $\Delta t$, $$dm(t)=(a_m(t)-a_m(t-\Delta t))/\Delta t;$$

calculating the relationship between the acceleration difference value $dc(t)$ of the first acceleration sensor and the actual output $s_c(t)$, $$dc(t)=k(s_c(t)-s_c(t-\Delta t));$$

calculating the relationship between the acceleration difference value $dm(t)$ of the second acceleration sensor and the actual output $s_m(t)$, $$dm(t)=k(s_m(t)-s_m(t-\Delta t)).$$

3. The automatic frame rate adjustment method of claim 1, wherein the step "calculating the mean value $\overline{Mc(t)}$ of the first differential modulus $Mc(t)$, and calculating the mean value $\overline{Mm(t)}$ of the second differential modulus $Mm(t)$" comprises:
    selecting a window with a width of L, calculating the mean value $\overline{Mc(t)}$ of the first differential modulus $Mc(t)$ in the window, $$\overline{Mc(t)}=\text{mean}(Mc(t-L:t)),$$

and calculating the mean value $\overline{Mm(t)}$ of the second differential modulus Mm(t) in the window, $$\overline{Mm(t)}=\text{mean}(Mm(t-L:t)).$$

4. The automatic frame rate adjustment method of claim 1, wherein after the step "calculating the mean value $\overline{Mc(t)}$ of the first differential modulus Mc(t), and calculating the mean value $\overline{Mm(t)}$ of the second differential modulus Mm(t)" further comprises:
presetting a dynamic threshold τ, determining that first acceleration sensor is stationary when the mean value $\overline{Mc(t)}$ of the first differential modulus Mc(t) is not greater than the dynamic threshold τ, and determining that the first acceleration sensor is not stationary when the mean value $\overline{Mc(t)}$ of the first differential modulus Mc(t) is greater than the dynamic threshold τ.

5. The automatic frame rate adjustment method of claim 4, wherein the range of the dynamic threshold τ is 0.005~0.01 m·s$^{-2}$.

6. The automatic frame rate adjustment method of claim 1, wherein after the step "determining the relative motion amplitude statem(t)=|$\overline{Mc(t)}$−$\overline{Mm(t)}$|" further comprises:
correcting the waveform of the relative motion amplitude statem(t);
wherein the step "correcting the waveform of the relative motion amplitude statem(t)" comprises:
selecting a window with a width of L;
calculating the difference value dMc(h) of the first differential modulus Mc(t) in the window, and $$dMc(h)=Mc(t-(L-1)\Delta t+h\Delta t)-Mc(t-(L-1)\Delta t+(h-1)\Delta t),$$
$$h=1,2\ldots,L-1;$$

calculating the difference value dMm(h) of the second differential modulus Mm(t) in the window, and $$dMm(h)=Mm(t-(L-1)\Delta t+h\Delta t)-Mm(t-(L-1)\Delta t+(h-1)\Delta t), h=1,2\ldots,L-1;$$

binarizing the difference value dMc(h) of the first differential modulus Mc(t) in the window and the difference value dMc(h) of the second differential modulus Mm(t) in the window, and recording them as a first binary difference value dMc(h)' and a second binary difference value dMc(h)', $$dMc(h)'=\begin{cases}0, & dMc(h)\leq 0\\1, & dMc(h)>0\end{cases}, dMm(h)'=\begin{cases}0, & dMm(h)\leq 0\\1, & dMm(h)>0\end{cases};$$

calculating the degree of similarity $R_p$ between the first binary difference value dMc(h)' and the second binary difference value dMc(h)', $0\leq R_p\leq 1$;
calculating the waveform comparison and correction item P(t) of the waveform, $$P(t)=\begin{cases}R_p, & \text{if } R_p<\alpha\\1, & \text{if } R_p\geq\alpha\end{cases}, 0<\alpha<1;$$

calculating P(t)●statem(t) and recording as a new relative motion amplitude statem(t).

7. The automatic frame rate adjustment method of claim 6, wherein $$R_p=\Sigma_{h=1}^{L-1}(|dMc(h)-dMm(h)|)/(L-1).$$

8. The automatic frame rate adjustment method of claim 6, wherein the value of α is 0.5.

9. The automatic frame rate adjustment method of claim 1, wherein q=4, f1 is 1 fps, f2 is 2 fps, f3 is 4 fps, f4 is 8 fps; T1 is statem(t)≤s$_1$, T2 is s$_1$<statem(t)≤s$_2$, T3 is s$_2$<statem(t)≤s$_3$, T4 is statem(t)>s$_3$, where s1 is 0.01 m·s$^{-2}$, s2 is 0.04 m·s$^{-2}$, s3 is 0.10 m·s$^{-2}$.

10. The automatic frame rate adjustment method of claim 1, further comprising:
adjusting the number of images taken at different frame rates in a cycle according to the frame rate $F_0(t)$;
wherein the step "adjusting the number of images taken at different frame rates in a cycle according to the frame rate $F_0(t)$" comprises:
obtaining the total number of images taken by the capsule endoscope in each cycle and recording as N(jT), recording the duration of each cycle as TS(s), where, 1≤j≤n, n is the total number of cycles;
calculating and allocating the number of images N1~Nq taken at the frame rates f1~fq, and N1~Nq meet the following conditions:

$$\sum_{i=1}^{q}N_i\leq N(jT),$$
$$\frac{1}{f_1}N_1+\frac{1}{f_2}N_2+\ldots+\frac{1}{f_q}N_q\geq T_s.$$

11. The automatic frame rate adjustment method of claim 10, further comprising:
allocating the total number of images to be taken for the remaining cycles based on the total number of images actually taken in a cycle;
wherein the step "allocating the total number of images to be taken for the remaining cycles based on the total number of images actually taken in a cycle" comprises:
calculating the total number of images N(jT)' actually taken in the j-th cycle;
calculating the total number of images $N_{maqin}$=N(jT)−N(jT)' in remaining to be taken in the j-th cycle;
calculating the total number of images $N(iT)_{new}$ taken in the remaining cycles, $$N(iT)_{new}=\frac{N_{maqin}}{n-j}+N(iT),$$

j<i≤n; N(iT) is the estimated total number of images taken in the original i-th cycle;
calculating again the number of images taken at different frame rates in each cycle.

12. A capsule endoscope system, comprising:
a capsule endoscope; and
an external device, comprising a memory and a processor, wherein the memory stores computer programs that run on the processor,
and the processor executes the computer programs to implement the steps in an automatic frame rate adjustment method, wherein the automatic frame rate adjustment method comprises:
receiving a first acceleration information $a_c(t)$ sensed by a first acceleration sensor in a capsule endoscope;
receiving a second acceleration information $a_m(t)$ sensed by a second acceleration sensor in an external device;
calculating and comparing the first acceleration information $a_c(t)$ and the second acceleration information $a_m(t)$ to obtain the relative motion amplitude statem(t) between the capsule endoscope and the external device;

adjusting the frame rate of the capsule endoscope according to the relative motion amplitude statem(t), wherein the larger the relative motion amplitude statem(t), the larger the frame rate $F_0(t)$, $$F_0(t) = \begin{cases} f1, & statem(t) \in T_1 \\ f2, & statem(t) \in T_2 \\ \vdots \\ f_q, & statem(t) \in T_q \end{cases}$$

wherein the step "calculating and comparing the first acceleration information $a_c(t)$ and the second acceleration information $a_m(t)$ to obtain the relative motion amplitude statem(t) between the capsule endoscope and the external device" comprises:
  performing a difference operation on the first acceleration information $a_c(t)$ to obtain a first acceleration difference value $d_c(t)$, and performing a difference operation on the second acceleration information $a_m(t)$ to obtain a second acceleration difference value $d_m(t)$;
  calculating the modulus of the first acceleration difference value $d_c(t)$ and recording it as a first differential modulus $Mc(t)=|d_c(t)|$, calculating the modulus of the second acceleration difference value $d_m(t)$ and recording it as a second differential modulus $Mm(t)=|d_m(t)|$;
  calculating the mean value $\overline{Mc(t)}$ of the first differential modulus $Mc(t)$, and calculating the mean value $\overline{Mm(t)}$ of the second differential modulus $Mm(t)$;
  determining the relative motion amplitude statem(t)=0 when the first acceleration sensor is stationary; determining the relative motion amplitude statem(t)=$|\overline{Mc(t)}-\overline{Mm(t)}|$ when the first acceleration sensor is not stationary.

13. A computer-readable storage medium, wherein the computer-readable storage medium stores computer programs,
  and the processor executes the computer programs to implement the steps in an automatic frame rate adjustment method, wherein the automatic frame rate adjustment method comprises:
    receiving a first acceleration information $a_c(t)$ sensed by a first acceleration sensor in a capsule endoscope;
    receiving a second acceleration information $a_m(t)$ sensed by a second acceleration sensor in an external device;
    calculating and comparing the first acceleration information $a_c(t)$ and the second acceleration information $a_m(t)$ to obtain the relative motion amplitude statem(t) between the capsule endoscope and the external device;
    adjusting the frame rate of the capsule endoscope according to the relative motion amplitude statem(t), wherein the larger the relative motion amplitude statem(t), the larger the frame rate $F_0(t)$, $$F_0(t) = \begin{cases} f1, & statem(t) \in T_1 \\ f2, & statem(t) \in T_2 \\ \vdots \\ f_q, & statem(t) \in T_q \end{cases}$$

wherein the step "calculating and comparing the first acceleration information $a_c(t)$ and the second acceleration information $a_m(t)$ to obtain the relative motion amplitude statem(t) between the capsule endoscope and the external device" comprises:
  performing a difference operation on the first acceleration information $a_c(t)$ to obtain a first acceleration difference value $d_c(t)$, and performing a difference operation on the second acceleration information $a_m(t)$ to obtain a second acceleration difference value $d_m(t)$;
  calculating the modulus of the first acceleration difference value $d_c(t)$ and recording it as a first differential modulus $Mc(t)=|d_c(t)|$, calculating the modulus of the second acceleration difference value $d_m(t)$ and recording it as a second differential modulus $Mm(t)=|d_m(t)|$;
  calculating the mean value $\overline{Mc(t)}$ of the first differential modulus $Mc(t)$, and calculating the mean value $\overline{Mm(t)}$ of the second differential modulus $Mm(t)$;
  determining the relative motion amplitude statem(t)=0 when the first acceleration sensor is stationary; determining the relative motion amplitude statem(t)=$|\overline{Mc(t)}-\overline{Mm(t)}|$ when the first acceleration sensor is not stationary.

* * * * *